United States Patent
Wang et al.

(10) Patent No.: US 10,031,118 B1
(45) Date of Patent: Jul. 24, 2018

(54) METHOD OF DETERMINING AND EVALUATING QUALITY OF PEANUT RAW MATERIAL SUITABLE FOR PROTEIN PROCESSING

(71) Applicant: Institute of Food Science and Technology, CAAS, Beijing (CN)

(72) Inventors: Qiang Wang, Beijing (CN); Hongzhi Liu, Beijing (CN); Aimin Shi, Beijing (CN); Li Liu, Beijing (CN); Hui Hu, Beijing (CN); Li Wang, Beijing (CN)

(73) Assignee: Institute of Food Science and Technology, CAAS, Beijing (CN)

( * ) Notice: Subject to any disclaimer, the term of this patent is extended or adjusted under 35 U.S.C. 154(b) by 0 days.

(21) Appl. No.: 15/671,877

(22) Filed: Aug. 8, 2017

(30) Foreign Application Priority Data

Jun. 20, 2017 (CN) .......................... 2017 1 0468727

(51) Int. Cl.
*G01N 33/02* (2006.01)
*G01N 33/68* (2006.01)

(52) U.S. Cl.
CPC ........... *G01N 33/025* (2013.01); *G01N 33/02* (2013.01); *G01N 33/68* (2013.01); *G01N 33/6803* (2013.01); *G01N 33/6827* (2013.01)

(58) Field of Classification Search
CPC .... G01N 33/02; G01N 33/025; G01N 27/447; G01N 2030/8831; G01N 2030/8818; G01N 33/68; G01N 33/6803; G01N 33/6806; G01N 33/6812; G01N 33/6827
See application file for complete search history.

(56) References Cited

FOREIGN PATENT DOCUMENTS

CN 102749420 B * 10/2014
CN 102879353 B 4/2016

OTHER PUBLICATIONS

Yu et al. "Peanut protein concentrate: Production and functional properties as affected by processing." Food Chemistry (2007) 103 121-129. (Year: 2007).*
Machine translation of CN 102749420 B, obtained from espacenet by the examiner on Sep. 12, 2017. (Year: 2017).*
Machine translation of CN 102749420 B, obtained from google patents by the examiner on Sep. 12, 2017. (Year: 2017).*
Parmar R.R., et al. (2011) Unified Approach in Food Quality Evaluation Using Machine Vision. In: Abraham A., et al. (eds) Advances in Computing and Communications. ACC 2011. Communications in Computer and Information Science, vol. 192. Springer, Berlin, Heidelberg. (Year: 2011).*
Luan, W. et al., "Study on the Main Traits of Peanut Varieties—Differences among Trait Performances and Types," Crop Germoplasm Resources, vol. 2, Available as Early as Jan. 1, 1986, 6 pages. (Submitted with Translation of Abstract).
Wan, S., "Peanut Quality (Excerpt)," Beijing: China Agricultural Science and Technology Press, Available as Early as Jan. 2007, 3 pages. (Submitted with Partial Translation).
Wang, L. et al., "Determining the contents of protein and amino acids in peanuts using near-infrared reflectance spectroscopy," Journal of the Science of Food and Agriculture, vol. 93, No. 1, Jan. 15, 2013, Published Online Jun. 12, 2012, 7 pages.
Wang, L. et al., "Protein Contents in Different Peanut Varieties and their Relationship to Gel Property," International Journal of Food Properties, vol. 17, No. 7, Published Online Nov. 4, 2013, 17 pages.

* cited by examiner

*Primary Examiner* — Christopher Adam Hixson
(74) *Attorney, Agent, or Firm* — McCoy Russell LLP

(57) ABSTRACT

A method of determining and evaluating quality of peanut raw material suitable for processing protein. The method includes the following step: determining fruit shape score, total protein content, leucine content, arginine content, conarachin I content and the mass percentage of the subunit with molecular weight of 23.5 kDa to total protein in the peanut sample to be tested; putting the determined values into formula (1) to obtain the protein powder quality of the peanut sample. The disclosure reduces the analysis step. The disclosure establishes the model of evaluating raw material quality for peanut protein processing, and the peanut protein powder quality can be determined by 6 peanut quality characteristics. The determination of indexes in the model can be predicted by the near infrared analyzer. Through the near infrared analysis of peanut kernel, the indexes in the model can be simultaneously predicted without any damage to the peanut kernel.

7 Claims, 1 Drawing Sheet

METHOD OF DETERMINING AND EVALUATING QUALITY OF PEANUT RAW MATERIAL SUITABLE FOR PROTEIN PROCESSING

CROSS-REFERENCE TO RELATED APPLICATION

The present application claims priority to Chinese Patent Application No. 201710468727.6, entitled "A METHOD OF DETERMINING AND EVALUATING QUALITY OF PEANUT RAW MATERIAL SUITABLE FOR PROTEIN PROCESSING," filed on Jun. 20, 2017, the entire contents of which are hereby incorporated by reference for all purposes.

TECHNICAL FIELD

The present disclosure relates to a method of determining and evaluating quality of peanut raw material suitable for protein processing.

BACKGROUND ART

Peanut (Arachis hypogaea L.) belongs to legumes and originated in tropical and subtropical regions of South America. China is the largest producer and consumer of peanut in the world. Peanut production was 16.44 million tons in 2015, of which 51% was for oil extraction. Peanut meal is a by-product after oil extraction and the annual output is 3 million tons. With about 44% of protein content, peanut meal is the world's third largest source of protein. But in the domestic market, peanut meal is mostly used for feed and has low added-value. At present, the market gap of vegetable protein in China is 1.35 million tons/year. Because the quality of peanut protein powder needs to be improved, its application in food processing is restricted. At present, there are many varieties of peanuts in China (more than 8,000 peanut germplasm are deposited), and the quality of protein in respective varieties is significantly different. Because the relationship between the raw material variety and protein quality is not clear, it lacks evaluation method and standard of processing suitability and peanut varieties are harvested and used in a mixed mode in the actual production. On the one hand, the product quality is decreased, and on the other hand, the cost is increased. So, it is urgent to establish a technology and method of evaluating quality of raw material suitable for peanut protein processing to screen the peanut varieties suitable for protein processing.

SUMMARY OF THE DISCLOSURE

The aim of the present disclosure is to provide a method of determining and evaluating quality of peanut raw material suitable for protein processing. By analyzing the relationship between peanut quality and protein processing, the present disclosure uses the supervised principal component regression analysis to establish the model of evaluating quality of peanut for protein and provide the theoretical basis for the utilization, identification and breeding of specialized peanut varieties.

The present disclosure provides a method of determining quality of peanut raw material suitable for protein processing, comprising the following steps:

determining the fruit shape score, total protein content, leucine content, arginine content, conarachin I content and the mass percentage of the subunit with molecular weight of 23.5 kDa to total protein in the peanut sample to be tested; wherein:

when the fruit shape of the peanut sample to be tested is hockey stick-shaped, the fruit shape score is 1; when the fruit shape of the peanut sample to be tested is hump-shaped, the fruit shape score is 2; when the fruit shape of the peanut sample to be tested is a string of beads-shaped, the fruit shape score is 3; when the fruit shape of the peanut sample to be tested is ordinary shape, the fruit shape score is 4; when the fruit shape of the peanut sample to be tested is wasp waist-shaped, the fruit shape score is 5; when the fruit shape of the peanut sample to be tested is calabash-shaped, the fruit shape score is 6; when the fruit shape of the peanut sample to be tested is cocoon-shaped, the fruit shape score is 7; when the fruit shape of the peanut sample to be tested is axe-shaped, the fruit shape score is 8;

determining the total protein content, leucine content and arginine content are the mass percentage of protein using near-infrared reflectance spectroscopy;

determining the conarachin I content is the mass percentage of conarachin I to total protein using near-infrared reflectance spectroscopy;

determining the mass percentage of subunit with molecular weight of 23.5 kDa to total protein using Sodium dodecyl sulfate-polyacrylamide gel electrophoresis and densitometric analysis. putting the above tested values into formula (1) to obtain the protein powder quality of the peanut sample to be tested;

peanut protein powder quality=1.656−0.046×fruit shape score+0.007×total protein content−0.91× leucine content+0.005×arginine content−0.013× conarachin I content−0.017×mass percentage of subunit with molecular weight of 23.5 kDa to total protein In the above method, the score of the fruit score is based on *Study on the Main Traits of Peanut Varieties-Differences among Trait Performances and Types* [J] (Luan Wenqi, Feng Haisheng and Wang Jingshan). When the fruit shape of the peanut varieties to be tested is not hockey stick-shaped, hump-shaped, a string of beads-shaped, wasp waist-shaped, calabash-shaped, cocoon-shaped or axe-shaped as being judged, then it is judged as ordinary shape.

In the above method, total protein content, leucine content and arginine content are measured based on the *Determining the contents of protein and amino acids in peanuts using near-infrared reflectance spectroscopy* [J] (Li Wang, Qiang Wang and Hongzhi Liu).

In the above method, the conarachin I content is measured by *Methods for detecting the content of protein components in peanut by near-infrared detection* [P] (Qiang Wang, Hongzhi Liu, Liu Li, Li Wang, Yin Du).

In the above method, the mass percentage of subunit with molecular weight of 23.5 kDa is measured based on *Protein contents in different peanut varieties and their relationship to gel property* [J] (Li Wang, Qiang Wang and Hongzhi Liu).

In the above method, the quality of the protein powder is a comprehensive evaluation result of the following quality: 10 indexes including fat content, crude fiber content, protein purity, ash content, hardness, elasticity, cohesion, water-holding capacity, oil-holding capacity and solubility.

The present disclosure further provides a method of evaluating quality of peanut raw material suitable for protein processing, comprising the following steps:

determining the protein powder quality of the peanut sample to be tested according to the above methods, and classifying the peanut sample to be tested according to the following criteria 1) to 3):

a. if the calculated value of peanut protein powder quality ≥76, then the peanut sample to be tested is suitable for protein powder processing;

b. if the calculated value of peanut protein powder quality is 67.5-76, then the peanut sample to be tested is substantially suitable for protein powder processing;

c. if the calculated value of peanut protein powder quality ≤67.5, the peanut sample to be tested is not suitable for protein powder processing.

The "suitable for protein powder processing" refers to the quality of the protein powder obtained by processing the peanut sample to be tested as raw material is relatively good and is suitable for the protein powder processing. The "substantially suitable for protein powder processing" refers to the quality of the protein powder obtained by processing the peanut sample to be tested as raw material is ordinary and is inferior to the quality of the protein powder obtained by processing the peanut sample suitable for protein processing as raw material, so it is substantially suitable for the protein powder processing. The "not suitable for protein powder processing" refers to the quality of the protein powder obtained by processing the peanut sample to be tested as raw material is relatively poor, especially the indexes such as hardness, elasticity, cohesion, water-holding capacity, oil-holding capacity and solubility are relatively poor, so it is not suitable for the protein powder processing.

The present disclosure has the following beneficial effects:

i. reducing the analysis steps, which is beneficial to enterprise application: for the determination of quality of peanut protein in the prior art, protein needs to be extracted, then a series of indexes are determined; in the method of the disclosure, the model of evaluating raw material quality for peanut protein processing is established, and the peanut protein powder quality can be determined by 6 peanut quality characteristics; the determination of indexes in the model, like amino acids etc., can be predicted by the near infrared analyzer, which is convenient and rapid; through the near infrared analysis of peanut kernel, the indexes in the model can be simultaneously predicted without any damage to the peanut kernel, and it is convenient and rapid; the simplified model only requires five indexes, which is simpler and can reflect many problems by using indexes as few as possible.

ii. raising product quality and promoting the development of agricultural products processing industry: high-quality peanut protein produced by using specialized varieties can be applied to processing of ham sausage, peanut milk and other products, improving its texture quality and providing a better feel when chewing; in addition, the standard of suitability for processing provides the basis for the establishment of the specialized enterprise variety planting base.

DETAILED DESCRIPTION OF EXAMPLES

Figure 1:
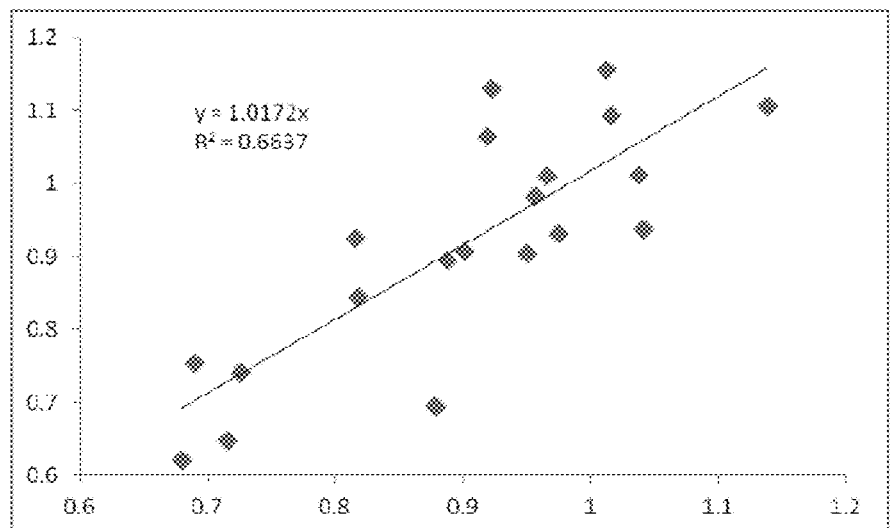
FIG. 1 shows the fitting chart of the original values and calculated values of the protein powder quality of 20 peanut samples in Example 2.

The experimental methods used in the following Examples are all conventional methods, unless otherwise specified.

The materials, reagents and the like used in the following Examples are all commercially available, unless otherwise specified.

Example 1. Establishment of Model for Determining Quality of Peanut Suitable for Protein Processing (1) Determination of Peanut Quality Taking peanut samples harvested in 2016 as a standard and 100 samples (in line with the normal distribution rule of peanut population, as shown in Table 1);

TABLE 1

| 100 peanut varieties | |
|---|---|
| No | Variety name |
| 1 | Zhonghua 8 |
| 2 | Shanhua 7 |
| 3 | Silihong |
| 4 | Luhua 11 |
| 5 | Bianhua 3 |
| 6 | Haihua 1 |
| 7 | Shuangji 2 |
| 8 | Shanhua 9 |
| 9 | Fenghua 5 |
| 10 | Yueyou 14 |
| 11 | Yueyou 45 |
| 12 | Yueyou 86 |
| 13 | Minhua 9 |
| 14 | Guihua 771 |
| 15 | Zhanhua 82 |
| 16 | Shanyou 250 |
| 17 | Longhua 243 |
| 18 | Heyou 11 |
| 19 | Zhenzhuhong |
| 20 | White peanut |
| 21 | Fenghua 1 |
| 22 | Fenghua 3 |
| 23 | Fenghua 4 |
| 24 | Xuhua 5 |
| 25 | Yuanhua 8 |
| 26 | Xuhua 13 |
| 27 | Huayu 20 |
| 28 | Huayu 23 |
| 29 | Huayu 28 |
| 30 | Huayu 31 |
| 31 | Baisha 1016 |
| 32 | Wucai peanut |
| 33 | Black peanut |
| 34 | 034-256-1 |
| 35 | Ji 9814 |
| 36 | Yuhua 15 |
| 37 | Yuhua 9326 |
| 38 | Yuhua 9327 |
| 39 | Kainong 30 |
| 40 | Kainong 37 |
| 41 | Yuanza 9102 |
| 42 | Zhongnong 108 |
| 43 | Quanhua 551 |
| 44 | Honghua 1 |
| 45 | Qinglan 8 |
| 46 | Huayu 8 |
| 47 | Luhua 14 |
| 48 | Xuhua 15 |
| 49 | Huayu 16 |
| 50 | Zhonghua 4 |
| 51 | Zhonghua 15 |
| 52 | Haiyu 6 |
| 53 | Lufeng 2 |

TABLE 1-continued 100 peanut varieties

| No | Variety name |
|---|---|
| 54 | Hongguan |
| 55 | Yuanza 9307 |
| 56 | Zhengnong 7 |
| 57 | Fenghua 6 |
| 58 | Luhua 9 |
| 59 | Luhua 15 |
| 60 | Xianghua 509-77 |
| 61 | Hua 17 |
| 62 | Jihua 4 |
| 63 | Jihua 5 |
| 64 | Jihua 8 |
| 65 | Jihua 9 |
| 66 | Jihua 10 |
| 67 | Jihua 12 |
| 68 | XY-1 |
| 69 | Huayu 16 |
| 70 | Huayu 19 |
| 71 | Huayu 25 |
| 72 | Huayu 33 |
| 73 | Huayu 36 |
| 74 | Puhua 28 |
| 75 | Puhua 9519 |
| 76 | Puzhenhua 1 |
| 77 | Yuhua 9502 |
| 78 | JS024 |
| 79 | JS0537 |
| 80 | Ningtai 9922 |
| 81 | Taihua 4 |
| 82 | Zhonghua 16 |
| 83 | XY-1 |
| 84 | Hongsha 1 |
| 85 | Huayu 36 |
| 86 | Huayu 39 |
| 87 | Huayu 51 |
| 88 | Huayu 52 |
| 89 | Luhua 12 |
| 90 | SH08 |
| 91 | SH09 |
| 92 | Gaoyou 1 |
| 93 | Gaoyou 3 |
| 94 | Hetian |
| 95 | Huayu 22 |
| 96 | Jiaokusi |
| 97 | Wujiaokusi |
| 98 | Xinjiang 1 |
| 99 | Xinjiang 3 |
| 100 | Xinjiang 4 |

The 45 indexes of each variety, such as sensory quality, physicochemical and nutritional quality and processing quality, are determined; wherein each index and the determination methods and standards thereof are as follows:

peanut physical traits: fruit shape: when the fruit shape of the peanut sample is hockey stick-shaped, the fruit shape score is 1; when the fruit shape of the peanut sample is hump-shaped, the fruit shape score is 2; when the fruit shape of the peanut sample is a string of beads-shaped, the fruit shape score is 3; when the fruit shape of the peanut sample is ordinary shape, the fruit shape score is 4; when the fruit shape of the peanut sample is wasp waist-shaped, the fruit shape score is 5; when the fruit shape of the peanut sample is calabash-shaped, the fruit shape score is 6; when the fruit shape of the peanut sample is cocoon-shaped, the fruit shape score is 7; when the fruit shape of the peanut sample is axe-shaped, the fruit shape score is 8; seed shape: see Study on the Main Traits of Peanut Varieties-Differences among Trait Performances and Types [J] (Luan Wenqi, 1986, Luan Wenqi, Feng Haisheng and Wang Jingshan, China Seed Industry, 1986, 23-7.); red skin: see Wan Shubo (Wan Shubo, 2008; Wan Shubo, Peanut Quality [M]. Beijing: China Agricultural Science and Technology Press, 2008); weight of 100 fruits: randomly taking 100 peanut fruits and weighing, then repeating 3 times for the average; weight of 100 kernels: randomly taking 100 peanut kernels and weighing, then repeating 3 times for the average;

analysis of physiochemical and nutritional quality of peanut: moisture content: GB/T 5009, 3-2003; fat content: GB/T 5009, 6-2003; protein content: GB/T 5009, 5-2003; ash content: GB/T 5009, 4-2003; crude fiber content: GB/T 5515-2008; amino acid content: GB/T 5009.124-2003; sugar content; protein subunit content: SDS-PAGE gel electrophoresis is used to determine the composition and content of protein subunits in these peanut varieties, the separation gel concentration is 13% and pH is 8.8; the concentration gel concentration is 5% and pH is 6.8; electrode buffer is 0.025 M Tris-HCl, 0.192 M glycine and 0.1% SDS, and the pH is 8.3; the gel after electrophoresis is photographed with the gel imaging system, US FlourChem V 2.0, and the relative content of each component is analyzed using Alpha Ease FC software; among the above indexes, the protein subunit content refers to the mass percentage of protein subunit to the protein, and the rest of the indexes refers to the mass percentage to peanut;

peanut processing quality analysis: protein extraction rate: the protein is extracted with the method of alkali-solution and acid-precipitation, and protein extraction rate=extracted protein mass/protein mass in peanuts×100%; kernel rate: weights of kernels obtained from 100 g of peanut fruits/100 g×100%;

The variation range, mean value, standard deviation, variation coefficient, upper quartile, median and lower quartile of the basic data of selected 61 peanut varieties are analyzed. The results are shown in Table 2.

TABLE 2

Quality Characteristics of Peanut Variety

| Factor | Variation range | Mean value | Standard deviation | Variation coefficient | Upper quartile | Median | Lower quartile |
|---|---|---|---|---|---|---|---|
| Fruit shape | 1.00-8.00 | 5.07 | 1.86 | 36.78 | 4.00 | 5.00 | 7.00 |
| Red skin | 1.00-9.00 | 5.47 | 1.46 | 26.62 | 5.00 | 6.00 | 6.00 |
| Seed shape | 1.00-5.00 | 2.40 | 1.79 | 74.54 | 1.00 | 1.00 | 5.00 |
| Weight of 100 fruits | 114.80-285.00 | 183.07 | 43.42 | 23.72 | 149.50 | 183.50 | 213.80 |
| Weight of 100 kernels | 38.6-120 | 72.16 | 18.64 | 25.83 | 57.75 | 71.90 | 85.20 |

TABLE 2-continued

Quality Characteristics of Peanut Variety

| Factor | Variation range | Mean value | Standard deviation | Variation coefficient | Upper quartile | Median | Lower quartile |
|---|---|---|---|---|---|---|---|
| Water content | 3.71-7.41 | 5.47 | 0.95 | 17.43 | 4.71 | 5.36 | 6.18 |
| Crude fat | 42.11-58.59 | 51.22 | 3.40 | 6.63 | 49.29 | 51.24 | 53.59 |
| Protein | 21.42-31.4 | 25.79 | 2.06 | 7.97 | 24.37 | 25.78 | 27.09 |
| Total sugar | 2.87-12.59 | 7.30 | 2.56 | 35.08 | 5.02 | 7.03 | 9.59 |
| Ash | 2.19-3.46 | 2.57 | 0.20 | 7.86 | 2.45 | 2.56 | 2.65 |
| Crude fiber | 1.5-6.9 | 2.53 | 0.82 | 32.28 | 2.10 | 2.50 | 2.80 |
| Total amino acids | 19.08-30.69 | 23.99 | 2.26 | 9.44 | 21.89 | 24.19 | 25.11 |
| Aspartic acid | 2.22-3.61 | 2.78 | 0.30 | 10.62 | 2.55 | 2.77 | 2.94 |
| Threonine | 0.40-0.87 | 0.63 | 0.08 | 12.76 | 0.59 | 0.62 | 0.68 |
| Serine | 0.81-1.42 | 1.10 | 0.11 | 10.45 | 1.04 | 1.10 | 1.16 |
| Glutamate | 2.05-6.12 | 4.36 | 0.66 | 15.14 | 4.00 | 4.36 | 4.71 |
| Proline | 0.79-1.70 | 1.21 | 0.21 | 17.62 | 1.0 | 1.16 | 1.36 |
| Glycine | 1.11-1.66 | 1.36 | 0.13 | 9.20 | 1.28 | 1.36 | 1.43 |
| Alanine | 0.63-1.38 | 0.90 | 0.17 | 18.58 | 0.77 | 0.91 | 1.00 |
| Cystine | 0.35-1.14 | 0.62 | 0.23 | 37.94 | 0.45 | 0.55 | 0.00 |
| Valine | 0.90-1.51 | 1.13 | 0.14 | 10.76 | 1.06 | 1.10 | 1.18 |
| Methionine | 0.09-0.71 | 0.32 | 0.14 | 43.56 | 0.22 | 0.28 | 0.38 |
| Isoleucine | 0.71-1.26 | 0.92 | 0.13 | 14.56 | 0.82 | 0.91 | 1.02 |
| Leucine | 1.28-1.99 | 1.61 | 0.19 | 11.76 | 1.46 | 1.64 | 1.74 |
| Tyrosine | 0.46-1.51 | 0.91 | 0.25 | 27.09 | 0.79 | 0.89 | 1.05 |
| Phenylalanine | 0.80-1.81 | 1.39 | 0.18 | 12.83 | 1.28 | 1.41 | 1.51 |
| Lysine | 0.77-1.15 | 0.97 | 0.09 | 8.80 | 0.90 | 0.97 | 1.03 |
| Histidine | 0.47-0.92 | 0.63 | 0.12 | 18.22 | 0.55 | 0.60 | 0.67 |
| Tryptophan | 0.16-0.42 | 0.24 | 0.05 | 19.22 | 0.22 | 0.24 | 0.26 |
| Arginine | 2.38-3.78 | 2.92 | 0.30 | 10.37 | 2.73 | 2.91 | 3.09 |
| Globulin | 47.60-73.02 | 59.68 | 6.11 | 10.24 | 54.45 | 58.70 | 64.77 |
| Conarachin | 26.99-52.20 | 40.34 | 6.15 | 15.25 | 35.23 | 41.30 | 45.75 |
| Conarachin I | 9.68-31.00 | 21.98 | 5.91 | 26.89 | 17.04 | 24.10 | 26.15 |
| Conarachin II | 14.70-21.90 | 18.36 | 1.89 | 10.28 | 16.90 | 18.05 | 19.84 |
| Globulin/Conarachin | 0.91-2.71 | 1.54 | 0.43 | 27.70 | 1.19 | 1.42 | 1.84 |
| 40.5 kDa | 7.73-14.50 | 10.36 | 1.60 | 15.42 | 9.32 | 10.14 | 11.40 |
| 37.5 kDa | 10.50-17.90 | 14.89 | 1.59 | 10.71 | 13.81 | 15.00 | 16.01 |
| 35.5 kDa | 0-19.20 | 10.21 | 5.22 | 51.17 | 10.85 | 12.30 | 13.17 |
| 23.5 kDa | 18.70-32.64 | 24.23 | 3.84 | 15.87 | 20.90 | 23.00 | 26.90 |
| 18 kDa | 2.12-11.40 | 7.22 | 2.82 | 39.08 | 4.48 | 7.76 | 9.40 |
| 17 kDa | 1.74-12.50 | 8.41 | 2.83 | 33.72 | 6.23 | 9.20 | 10.50 |
| 15.5 kDa | 2.33-11.90 | 6.35 | 2.18 | 34.29 | 4.93 | 6.40 | 7.75 |
| Protein extraction rate (%) | 59.51-88.97 | 74.00 | 5.78 | 7.81 | 70.71 | 74.63 | 77.57 |

TABLE 2-continued

Quality Characteristics of Peanut Variety

| Factor | Variation range | Mean value | Standard deviation | Variation coefficient | Upper quartile | Median | Lower quartile |
|---|---|---|---|---|---|---|---|
| Kernel rate (%) | 50.31-79.94 | 69.93 | 5.94 | 8.50 | 66.06 | 70.02 | 74.08 |

The variation coefficient is a statistical magnitude for measuring variation degree in a set of data. The variation coefficients of fat content, protein content, ash content, total amino acid content, glycine content, lysine content, protein extraction rate, kernel rate is <10% (6.63%, 7.97%, 7.86%, 9.44%, 9.20%, 8.80%, 7.81%, 8.50%, respectively), and low variation coefficients indicate small dispersion degrees. The variation coefficients of other indexes are relatively high, indicating relatively large differences existing in many qualities of different peanut varieties. With comparison of mean values and median, it can be found that except that the differences of seed shape and 35.5 kDa content is 58.33% and 20.50% respectively, the median of other qualities are close to their mean values, indicating outliers in these data is relatively few.

(2) Determination of Peanut Protein Powder Quality

Peanut protein powder quality includes: 10 indexes including fat content, crude fiber content, protein purity, ash content, hardness, elasticity, cohesion, water-holding capacity, oil-holding capacity and solubility, and they are calculated according to the following formula:

peanut protein powder quality=0.012×fat content+ 0.090×crude fiber content−0.210×protein purity+0.300×ash content+0.1618×hardness+ 0.3781×elasticity+1.1573×cohesion−0.035×water-holding capacity-0.320×oil-holding capacity-0.469×solubility;

fat content: GB/T 5009, 6-2003; crude fiber content: GB/T 5515-2008; all the above content refers to the mass percentage to peanut; protein purity: protein content/protein mass in protein powder×100%; ash content GB/T 5009, 4-2003;

water-holding capacity of protein: the determination uses the improved method of Beuchat L. R. (1977); the specific method is as follows:

1) accurately taking 1.000 g samples into a centrifuge tube and weighing; then adding 10 mL of distilled water to prepare 10% protein solution;

2) vibrating with vertical movements for 5 min such that all proteins are homogeneously dispersed; after standing at room temperature for 30 min, centrifuging at 3000 r/min for 20 min; carefully removing the supernatant and then weighing; the computational formula of water binding capability is as follows:

$$WBC = \frac{W_2 - W_1}{W_0};$$

wherein $W_0$ is protein mass, g; $W_1$ is the weight of the centrifuge tube, g; $W_2$ is the weight of centrifuge tube after removing the supernatant, g;

oil-holding capacity of protein: the improved method of Chakraborty P. (1986) is used; the specific method is as follows:

accurately taking 1.000 g samples into a centrifuge tube and weighing; then adding 5 mL of soybean salad oil;

vibrating with vortical movements for 5 min such that all proteins are homogeneously dispersed; after standing at room temperature for 30 min, centrifuging at 3000 r/min for 20 min; removing the supernatant salad oil and then weighing. The computational formula of fat binding capability is as follows:

$$FBC = \frac{W_2 - W_1}{W_0};$$

wherein each symbol is the same as the WBC formula;

protein solubility: accurately weighing 1.000 g peanut protein (N) (protein purity is P) into a triangular flask and adding 40 mL of distilled water before shaking homogeneously; placing in 30° C. constant temperature water bath oscillator, vibrating at 150 r/min for 120 min, and then transferring the mixture to 50 mL (V1) volumetric flask before adding water to constant volumes; then standing for 5 min and taking the supernatant to centrifugate at 1500 r/min for 10 min, and then filtering the supernatant with quantitative filter paper; taking 15 mL (V2) into a digestion tube and concentrating in an oven at 150° C. for 120 min; then using Kjeldahl Nitrogen to determine the concentration (C, mg/mL). The computational formula of nitrogen solubility index is as follows:

$$NSI = \frac{C \times \frac{V_1}{V_2}}{P \times N} \times 100$$

TABLE 3

Quality Characteristics of 100 Peanut Protein Powders

| | Variation range | Mean value | Standard deviation | Upper quartile | Median | Lower quartile | Variation coefficient/% | Data becoming poor/% |
|---|---|---|---|---|---|---|---|---|
| Ash | 0.74-2.35 | 1.35 | 0.32 | 1.11 | 1.32 | 1.50 | 24.09 | 2.22 |
| Crude fat | 0.54-8.84 | 2.52 | 1.60 | 1.35 | 2.26 | 3.26 | 63.56 | 10.32 |
| Crude fiber | 0.00-1.02 | 0.28 | 0.22 | 0.14 | 0.23 | 0.34 | 77.57 | 17.86 |

TABLE 3-continued

Quality Characteristics of 100 Peanut Protein Powders

|  | Variation range | Mean value | Standard deviation | Upper quartile | Median | Lower quartile | Variation coefficient/% | Data becoming poor/% |
|---|---|---|---|---|---|---|---|---|
| Protein purity | 85.64-94.81 | 90.57 | 1.90 | 89.44 | 90.51 | 91.89 | 2.10 | 0.07 |
| Water-holding capacity | 0.74-1.38 | 1.07 | 0.18 | 0.94 | 1.08 | 1.23 | 16.90 | 0.93 |
| Oil-holding capacity | 1.04-1.71 | 1.34 | 0.12 | 1.26 | 1.33 | 1.42 | 8.89 | 0.75 |
| Hardness | 0.37-4.26 | 1.60 | 0.86 | 0.91 | 1.60 | 2.09 | 53.37 | 0.00 |
| Elasticity | 0.53-0.97 | 0.75 | 0.11 | 0.68 | 0.75 | 0.82 | 15.09 | 0.00 |
| Cohesion | 0.28-0.59 | 0.39 | 0.06 | 0.35 | 0.39 | 0.43 | 15.04 | 0.00 |
| Solubility | 57.63-93.44 | 79.33 | 9.43 | 81.91 | 80.12 | 76.76 | 11.89 | 0.97 |

(3) Establishing the Model of Evaluating Quality of Peanut Protein Powder with the Supervised Principal Component Analysis The supervised principal component analysis does not use all the regression independent variables to establish model, and it only uses the independent variables which have strong correlation with the corresponding variables. According to the correlation coefficient between the corresponding variable and each independent variable, the regression independent variable set is screened. The independent variables with the correlation coefficient exceeding a certain threshold are screened out, and then the principal component regression analysis on the partial regression independent variables which are newly screened out are carried out. The supervised principal component regression analysis is carried out to establish the model for the first 80 varieties in selected 100 varieties.

1. Independent Variable Analysis (Peanut Quality)

The outliers of peanut quality (for No. 2, 17 and 23 peanut varieties) are removed using Boxplot method, so the remaining 38 varieties are analyzed.

2. Screening Evaluation Indexes of Peanut Quality

According to concept of regression analysis, the regression coefficient significance analysis is carried out for single index of peanut quality and protein quality and it is found that 6 indexes have significant correlation at 0.01 level with the protein powder quality.

TABLE 4

Regression Significance Index Table of Peanut Quality and Protein Powder Quality

| No. | Index | P value |
|---|---|---|
| 1 | Fruit shape | 0.011 |
| 2 | Crude protein | 0.010 |
| 3 | Crude fiber | 0.018 |
| 4 | Leucine | 0.009 |
| 5 | Arginine | 0.005 |
| 6 | Conarachin I | 0.003 |
| 7 | 23.5 kDa | 0.001 |

3. Principal Component Analysis

Principal component analysis and dimensionality reduction on the 6 screened indexes are carried out, as shown in Table 5.

TABLE 5

The Eigenvalues of Correlation Matrix

|  | Variance contribution ratio/% | Cumulative variance contribution ratio/% |
|---|---|---|
| 1 | 45.09 | 45.09 |
| 2 | 21.52 | 66.61 |
| 3 | 15.66 | 82.27 |
| 4 | 7.81 | 90.07 |
| 5 | 6.21 | 96.28 |

Through the principal component analysis, it is found that the cumulative contribution rate of the first 3 principal components is 82.27%. Therefore, the first 3 principal components can express the original principal component information, and the original 6 indexes are transformed into 3 new indexes, playing the role of dimensionality reduction. SAS is used to output the eigenvectors (not listed here) of the first 3 principal components, and the linear relationship between the first 3 principal components and each index. The relational expression between each principal component and each independent variable is used to calculate each principal component score. Each principal component score of each evaluation object can be obtained by putting the normalized data into each relational expression, as shown in Table 6.

TABLE 6

Each Principal Component Score

| No. | Principal component 1 | Principal component 2 | Principal component 3 |
|---|---|---|---|
| 1 | 0.33513 | −0.04893 | −1.82966 |
| 2 | 0.90626 | −0.24662 | −2.74372 |
| 3 | −2.38043 | −0.35297 | −0.22615 |
| 4 | −1.05145 | 1.72192 | −1.70074 |
| 5 | −1.828 | −0.3175 | 0.2592 |
| 6 | −197085 | 0.31743 | −0.52289 |
| 7 | −0.6035 | −1.97114 | −1.00505 |
| 8 | −2.28598 | 1.67866 | 0.51693 |
| 9 | −0.64892 | 1.5006 | 0.14137 |

TABLE 6-continued

Each Principal Component Score

| No. | Principal component 1 | Principal component 2 | Principal component 3 |
|---|---|---|---|
| 10 | 1.07462 | 0.92645 | −0.10074 |
| 11 | 0.3344 | 1.20402 | −0.12344 |
| 12 | 0.26419 | 0.95198 | 0.65105 |
| 13 | 0.0007 | −0.25002 | −1.04761 |
| 14 | −0.00738 | 1.08647 | 1.57252 |
| 15 | 0.322 | 1.37846 | 0.56167 |
| 16 | −0.12353 | −0.19127 | −0.99232 |
| 17 | 0.81486 | 1.80951 | −0.27637 |
| 18 | 0.39675 | 0.62271 | 1.02459 |
| 19 | −0.865 | −0.65647 | −1.33418 |
| 20 | −0.12587 | −0.77792 | −1.23228 |
| 21 | 1.28274 | −0.77738 | 0.38345 |
| 22 | 0.56524 | −0.25049 | −0.04527 |
| 23 | 0.84427 | −1.07593 | 0.3657 |
| 24 | 1.56148 | 0.56384 | −0.10501 |
| 25 | −0.2038 | −0.02885 | −0.16002 |
| 26 | 0.85122 | 0.57793 | 0.82137 |
| 27 | 0.2339 | −1.69847 | 1.52744 |
| 28 | 0.73286 | 0.8857 | −0.25135 |
| 29 | 1.39272 | −0.25378 | 0.31745 |
| 30 | 0.02028 | 0.15063 | 1.20141 |
| 31 | 1.29556 | −0.42034 | −0.11298 |
| 32 | 0.87203 | −0.60832 | −0.66893 |
| 33 | −0.85097 | −1.10865 | 0.37452 |
| 34 | −0.9059 | −1.65452 | 1.20532 |
| 35 | −0.37831 | −0.0617 | 1.74358 |
| 36 | −0.34961 | −1.18449 | 0.30082 |
| 37 | 0.58504 | −1.17134 | 0.23583 |
| 38 | −0.10674 | −0.26919 | 1.27448 |

TABLE 7

Regression Coefficient Significance

| Variable | Coefficient | P value |
|---|---|---|
| Intercept | 0.994 | 0.01 |
| PC1 | $-0.1232 \times 10^{-6}$ | 0.737 |
| PC2 | −0.008 | 0.035 |
| PC3 | −0.50 | 0.045 |

Example 2. Determination of Peanut Protein Powder Quality

The remaining 20 peanut varieties of Example 1 are subjected to protein powder quality determination.

The fruit shape score, crude protein content, leucine content, arginine content, conarachin I and the mass percentage of the subunit with molecular weight of 23.5 kDa of the 20 peanut varieties are put into formula (1) to calculate the protein powder quality of the 20 varieties. The comparison between the model prediction value and the chemical measurement value of the peanut protein powder quality is shown in Table 8; and the regression analysis on the calculated result of the model and the determined protein powder quality is carried out, and the correlation coefficient is 0.815, as shown in FIG. 1.

TABLE 8

Comparison of Model Prediction Value and Chemical Measure Value of Peanut Protein Powder Quality

| Peanut variety | Original value | Calculated value | Absolute error | Relative error/% |
|---|---|---|---|---|
| 1 | 0.956366 | 0.982096 | 0.02573 | 2.690405768 |
| 2 | 0.878048 | 0.694 | 0.184048 | 20.96101604 |
| 3 | 1.138497 | 1.105532 | 0.032965 | 2.895482134 |
| 4 | 0.975065 | 0.931867 | 0.043198 | 4.430309178 |
| 5 | 0.950299 | 0.903721 | 0.046578 | 4.901405643 |
| 6 | 1.01263 | 1.156137 | 0.143507 | 14.17170433 |
| 7 | 0.816033 | 0.925182 | 0.109149 | 13.37556937 |
| 8 | 1.041211 | 0.938321 | 0.10289 | 9.881798557 |
| 9 | 0.68934 | 0.752932 | 0.063592 | 9.225008988 |
| 10 | 0.887131 | 0.89405 | 0.006919 | 0.77990647 |
| 11 | 0.900956 | 0.906679 | 0.005723 | 0.635244245 |
| 12 | 1.01584 | 1.093221 | 0.077381 | 7.617481622 |
| 13 | 0.922367 | 1.130256 | 0.207889 | 22.53865526 |
| 14 | 0.818072 | 0.845398 | 0.027326 | 3.340253518 |
| 15 | 0.965279 | 1.00908 | 0.043801 | 4.537611922 |
| 16 | 0.72536 | 0.740208 | 0.014848 | 2.046986087 |
| 17 | 1.038059 | 1.011532 | 0.026527 | 2.555429174 |
| 18 | 0.71568 | 0.648147 | 0.067533 | 9.436219609 |
| 19 | 0.67934 | 0.621112 | 0.058228 | 8.57119107 |
| 20 | 0.918874 | 1.063923 | 0.145049 | 15.78546674 |

4. Establishment of Regression Equation

The regression analysis showed that the regression coefficients of principal components 2 and 3 and protein powder quality are significant at 0.05 level (as shown in Table 7). Therefore, the relationship between principal components 2 and 3 and the protein powder quality is established, and the relationship between each index and protein powder quality is further established. The result is shown in the formula (1).

Example 3. Establishment of Method of Evaluating Peanut Quality Suitable for Protein Processing By using K-means clustering analysis and the actual situation, the protein powder quality of 100 peanut varieties is classified into two groups, suitable and substantially suitable (Table 9).

TABLE 9

Suitability Analysis of Protein Powder Processing

| Class-ification | Stand-ard | Number of sample | Sample name |
|---|---|---|---|
| Suitable | ≥1.08 | 14 | Luhua 11, Shuangji 2, Bianhua 3, Fenghua 1, Kainong 30, Feng Hua 3, Shanhua 7, Minhua 9, Zhanhua 82, Yuhua 15, Haihua 1, Honghua 1, Ji 9814, and Yueyou 14 |
| Substantially suitable | 0.85-1.08 | 34 | 034-256-1, Shanhua 9, Huayu 16, Luhua 9, Kainong 37, Lufeng 2, Luhua 14, Zhonghua 8, Guihua 771, Shanyou 250, Xuhua 13, Qinglan 8, Silihong, Fenghua 5, Huayu 23, Zhengong 7, Zhongnong 108, Huayu 8, Yuanhua 8, Hongguan, hua 17, Zhenzhuhong, Huayu 20, Haiyu 6, Yuhua 9327, Longhua 243, Heyou 11, black peanut, Zhonghua 15, Yueyou 86, white peanut, Yuhua 9326, Quanhua 551, and Xuhua 5 |

The remaining 52 varieties are not suitable.

According to the regression coefficient, the weight of each index is determined. By using K-means clustering analysis and the actual situation, each evaluation index is classified into Class I, Class II and Class III, and the weight value of each index is used as Class I score, and so on.

TABLE 10

Weight of Each Index in Formula (1)

| No | Index | Weight |
|---|---|---|
| 1 | Fruit shape | 12 |
| 2 | Crude protein | 16 |
| 3 | Leucine | 12 |
| 4 | Arginine | 17 |
| 5 | Conarachin I | 21 |
| 6 | 23.5 kD | 22 |

The 6 quality indexes of peanut are analyzed by K-means clustering, and each index is classified into 3 categories: Class I (suitable), Class II (substantially suitable) and Class III (not suitable). The weight of each index is used as the highest score, i.e., Class I, and so on, and the corresponding scores are given to each level of index, as shown in Table 11.

TABLE 11

Scores of Each Index at Each Level

| Index | | Class I | Class II | Class III |
|---|---|---|---|---|
| Fruit shape− | Category value | ≤3 | 3-6.54 | >6.54 |
| | Score | 12 | 8 | 4 |
| Crude protein+ | Category value | ≥27.13 | 24.27-27.13 | <24.27 |
| | Score | 16 | 12 | 8 |
| Leucine− | Category value | ≤1.39 | 1.39-1.66 | >1.66 |
| | Score | 12 | 8 | 4 |
| Arginine+ | Category value | ≥3.70 | 3.00-3.70 | <3.30 |
| | Score | 17 | 13 | 9 |
| Conarachin I+ | Category value | ≥29.04 | 23.63-29.04 | <23.63 |
| | Score | 21 | 16 | 11 |
| 23.5 kDa− | Category value | ≤20.80 | 20.80-23.72 | >23.72 |
| | Score | 22 | 17 | 12 |

The sum of each trait index score is used as the final score of each peanut variety. According to the K-means clustering analysis formula, the final score of each variety is classified into 3 categories: Class I (suitable), Class II (substantially suitable) and Class III (not suitable), as shown in Table 12.

TABLE 12

Classification of Peanut Variety Based on K-means Clustering Analysis Method

| Classifi-cation | Standard | Number of sample | Sample name |
|---|---|---|---|
| Suitable | ≥76 | 11 | Luhua 11, Shuangji 2, Bianhua 3, Fenghua 1, Honghua 1, Luhua 14, Kainong 30, Zhanhua 82, Minhua 9, Yueyou 14, Yuhua 15, and Ji 9814 |
| Substantially suitable | 67.5-76 | 35 | Fenghua 3, Haiyu 6, Shanhua 9, Shanyou 250, Zhenzhuhong, Yuanhua 8, 034-256-1, Feng Hua 3, Lufeng 2, Shuangji 2, Hongguan, Fenghua 6, Haihua 1, Silihong, Quanhua 551, Huayu16, white peanuts, Fenghua 1, Zhongnong 108, Qinglan 8, Yuhua 9326, Yuhua 9327, Guihua 771, Xuhua 13, Yueyou 86, Heyou 11, Kainong 37, Huayu 31, Hua 17, Huayu 20, Zhonghua 8, and Luhua 15 |

The remaining 54 varieties are not suitable.

The results of Table 11 are compared with the results in Table 12, and the matching degree is: suitable varieties account for 92.6%, substantially suitable varieties account for 84.7% and not suitable varieties account for 71.2%, indicating that the evaluation results are relatively good and suitable for being used as evaluation standard of peanut quality suitable for processing protein powder.

Figure 2:
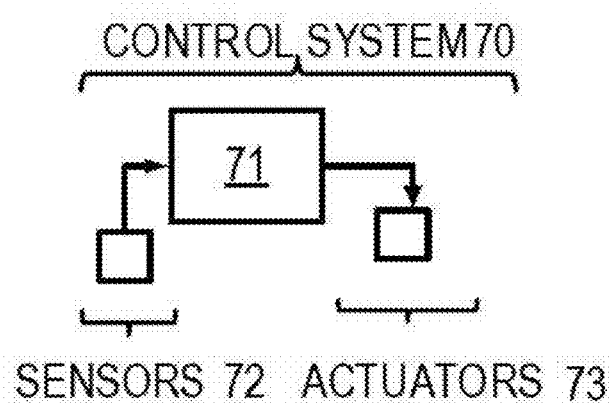
FIG. 2 shows a control system programmed with instructions to perform the methods and operations described herein.

Referring to FIG. 2, a control system 70 including controller 71 is shown. Controller 71 may receive various signals from sensors 72, and send control signals to various actuators 73. The various sensors may include, for example, a camera. The various actuators may include a sorting machine, for example. The controller 71 may send a signal to the sorting machine. Controller 71 may be a microcomputer, including a microprocessor unit, input/output ports, an electronic storage medium for executable programs and calibration values. Controller 71 may be programmed with computer readable data representing instructions executable to perform the methods described herein as well as variants that are anticipated but not specifically listed. The control system may be part of a processing plant and be coupled with transporter devices, sorting machines, inspection machines, and the like. The system may be programmed to carry out the quality determination and take actions responsive thereto, such as adjusting transportation of the inspected element via actuation of one or more actuators via the controller without human intervention, and thereby provide efficient processing of the image data of the element to be inspected and thus fast and accurate quality determination.

In one example, a method for automatically processing protein power may include, via a processor having instructions stored in memory and in communication with sensors and actuators, the instructions for determining quality of peanut raw material suitable for protein processing, including determining fruit shape score, total protein content, leucine content, arginine content, conarachin I content and the mass percentage of the subunit with molecular weight of 23.5 kDa to total protein in a peanut sample to be tested from one or more sensed parameters sensed by a sensor contacting or sensing the raw material; wherein when the fruit shape of the peanut sample to be tested is determined to be hockey stick-shaped sensed via a camera for example and determined via the instructions analysing image data from the camera, the fruit shape score is 1; when the fruit shape of the peanut sample to be tested is determined to be hump-shaped, the fruit shape score is 2; when the fruit shape of the peanut sample to be tested is determined to be a string of beads-shaped, the fruit shape score is 3; when the fruit shape of the peanut sample to be tested is ordinary shape, the fruit shape score is 4; when the fruit shape of the peanut sample to be tested is wasp waist-shaped, the fruit shape score is 5; when the fruit shape of the peanut sample to be tested is calabash-shaped, the fruit shape score is 6; when the fruit shape of the peanut sample to be tested is cocoon-shaped, the fruit shape score is 7; when the fruit shape of the peanut sample to be tested is axe-shaped, the fruit shape score is 8. The shape determination via the image processing instructions in the processor may be based on taking camera image data and first determining an outline of the peanut compared with a contrasting background of a known color (e.g., via thresholding each pixel value) and then processing the detected edge and categorizing the resulting shape into only one and exactly one of the options listed above so that the shape is uniquely identified. The instructions may further include that the total protein content, leucine content and arginine content are the mass percentage of protein, leucine and arginine to the peanut sample to be tested respectively, where these parameters may be determined by near-infrared reflectance spectroscopy sensors.

The instructions may further include that the conarachin I content is the mass percentage of conarachin I to total protein, which may be determined by Sodium dodecyl sulfate-polyacrylamide gel electrophoresis and densitometric analysis or related sensors. The instructions may put the above determined values into formula (1) stored in memory to obtain the protein powder quality of the peanut sample to be tested and display the determined quality and/or transmit the determined quality to another electronic system, and may include adjusting an actuator such as a sorting machine based on the determined quality. Further, in one example, peanut protein powder quality=1.656−0.046×fruit shape score+0.007×total protein content−0.91×leucine content+0.005×arginine content−0.013×conarachin I content−0.017×mass percentage of subunit with molecular weight of 23.5 kDa to total protein, which may be stored in the memory. Instruction may also include classifying the peanut sample to be tested according to the following criteria 1) to 3):

1) if the calculated value of the peanut protein powder quality ≥76, then the peanut sample to be tested is suitable for protein powder processing and directed along a first path via an actuator for the processing;

2) if the calculated value of the peanut protein powder quality is 67.5-76, then the peanut sample to be tested is substantially suitable for protein powder processing but directed along a second path via the actuator; and 3) if the calculated value of the peanut protein powder quality ≤67.5, the peanut sample to be tested is not suitable for protein powder processing and directed along a third path via the actuator, which may be a sorting machine vane or other component to direct the raw material along a processing path in processing equipment.

The invention claimed is:

1. A method of determining quality of peanut raw material suitable for protein processing, comprising:
with a controller, determining each of a fruit shape score, a total protein content, a leucine content, an arginine content, a conarachin I content, and a mass percentage of a subunit with a molecular weight of 23.5 kDa to total protein in a peanut sample to be tested,
wherein determining the fruit shape score comprises obtaining image data from a camera, and with the controller, analyzing the image data, the analyzing including categorizing a fruit shape of the peanut sample, and wherein when the fruit shape of the peanut sample is categorized as hockey stick-shaped, the fruit shape score is 1; when the fruit shape of the peanut sample is categorized as hump-shaped, the fruit shape score is 2; when the fruit shape of the peanut sample is categorized as string of beads-shaped, the fruit shape score is 3; when the fruit shape of the peanut sample is categorized as an ordinary shape, the fruit shape score is 4; when the fruit shape of the peanut sample is categorized as wasp waist-shaped, the fruit shape score is 5; when the fruit shape of the peanut sample is categorized as calabash-shaped, the fruit shape score is 6; when the fruit shape of the peanut sample is categorized as cocoon-shaped, the fruit shape score is 7; and when the fruit shape of the peanut sample is categorized as axe-shaped, the fruit shape score is 8,
wherein the total protein content, leucine content, and arginine content are mass percentages of protein, leucine, and arginine to the peanut sample respectively,
wherein the conarachin I content is a mass percentage of conarachin I to total protein,
wherein the method further comprises, with the controller, putting the above determined values into the following equation to obtain a protein powder quality of the peanut sample: peanut protein powder quality=1.656−0.046×fruit shape score+0.007×total protein content−0.91×leucine content+0.005×arginine content−0.013×conarachin I content−0.017×mass percentage of the subunit with the molecular weight of 23.5 kDa to total protein,
wherein the method further comprises, with the controller, displaying the peanut protein powder quality and/or transmitting the peanut protein powder quality to another electronic system, and adjusting an actuator based on the determined quality.

2. A control system for determining quality of peanut raw material suitable for protein processing, comprising:
a controller for receiving signals from sensors and sending control signals to actuators, wherein the control system is programmed with computer readable data representing instructions executable to:
determine each of a fruit shape score, a total protein content, a leucine content, an arginine content, a conarachin I content, and a mass percentage of a subunit with a molecular weight of 23.5 kDa to total protein in a peanut sample to be tested, wherein determining the fruit shape score comprises obtaining image data from a camera; and
analyze the image data, including categorizing a fruit shape of the peanut sample, wherein when the fruit shape of the peanut sample is categorized as hockey stick-shaped, the fruit shape score is 1; when the fruit shape of the peanut sample is categorized as hump-shaped, the fruit shape score is 2; when the fruit shape of the peanut sample is categorized as string of beads-shaped, the fruit shape score is 3; when the fruit shape of the peanut sample is categorized as an ordinary shape, the fruit shape score is 4; when the fruit shape of the peanut sample is categorized as wasp waist-shaped, the fruit shape score is 5; when the fruit shape of the peanut sample is categorized as calabash-shaped, the fruit shape score is 6; when the fruit shape of the peanut sample is categorized as cocoon-shaped, the fruit shape score is 7; and when the fruit shape of the peanut sample is categorized as axe-shaped, the fruit shape score is 8, wherein the total protein content, leucine content, and arginine content are mass percentages of protein, leucine, and arginine to the peanut sample, respectively, wherein the conarachin I content is a mass percentage of conarachin I to total protein, wherein the instructions further comprise instructions executable to put the above determined values into the following equation to obtain a protein powder quality of the peanut sample: peanut protein powder quality=1.656−0.046×fruit shape score+0.007×total protein content−0.91×leucine content+0.005×arginine content−0.013×conarachin I content−0.017×mass percentage of the subunit with the molecular weight of 23.5 kDa to total protein, and instructions executable to take actions responsive to the peanut protein powder quality, wherein the actuators include a sorting machine, and wherein the controller is configured to send a signal to the sorting machine, the signal based on the peanut protein powder quality.

3. A method of determining quality of peanut raw material suitable for protein processing, comprising:

with a controller, determining each of a fruit shape score, a total protein content, a leucine content, an arginine content, a conarachin I content, and a mass percentage of a subunit with a molecular weight of 23.5 kDa to total protein in a peanut sample to be tested, wherein determining the fruit shape score comprises obtaining image data from a camera, and with the controller, analyzing the image data, the analyzing including categorizing a fruit shape of the peanut sample, and wherein when the fruit shape of the peanut sample is categorized as hockey stick-shaped, the fruit shape score is 1; when the fruit shape of the peanut sample is categorized as hump-shaped, the fruit shape score is 2; when the fruit shape of the peanut sample is categorized as string of beads-shaped, the fruit shape score is 3; when the fruit shape of the peanut sample is categorized as an ordinary shape, the fruit shape score is 4; when the fruit shape of the peanut sample is categorized as wasp waist-shaped, the fruit shape score is 5; when the fruit shape of the peanut sample is categorized as calabash-shaped, the fruit shape score is 6; when the fruit shape of the peanut sample is categorized as cocoon-shaped, the fruit shape score is 7; and when the fruit shape of the peanut sample is categorized as axe-shaped, the fruit shape score is 8, wherein the total protein content, leucine content, and arginine content are mass percentages of protein, leucine, and arginine to the peanut sample respectively, wherein the conarachin I content is a mass percentage of conarachin I to total protein, wherein the method further comprises, with the controller, putting the above determined values into the following equation to obtain a protein powder quality of the peanut sample: peanut protein powder quality=1.656−0.046×fruit shape score+0.007×total protein content−0.91×leucine content+0.005×arginine content−0.013×conarachin I content−0.017×mass percentage of the subunit with the molecular weight of 23.5 kDa to total protein, wherein the method further comprises, with the controller, displaying the peanut protein powder quality and/or transmitting the peanut protein powder quality to another electronic system, and wherein the method further comprises, with the controller, taking actions responsive to the peanut protein powder quality, the actions including adjusting transportation of the peanut sample via actuation of one or more actuators without human intervention.

4. The method of claim 3, wherein the one or more actuators include a transporter device, a sorting machine, and/or an inspection machine.

5. A method of evaluating quality of peanut raw material suitable for protein processing, comprising:

determining protein powder quality of a peanut sample to be tested according to the method of claim 1, and with the controller, classifying the peanut sample according to the following criteria 1) to 3):

1) if a calculated value of the peanut protein powder quality ≥76, then the peanut sample is suitable for protein powder processing;

2) if the calculated value of the peanut protein powder quality is 67.5-76, then the peanut sample is substantially suitable for protein powder processing;

3) if the calculated value of the peanut protein powder quality ≤67.5, the peanut sample is not suitable for protein powder processing, wherein:

if the peanut sample is classified as suitable for protein powder processing, with the controller, sending a signal to an actuator to direct the peanut sample along a first path;

if the peanut sample is classified as substantially suitable for protein powder processing, with the controller, sending a signal to the actuator to direct the peanut sample along a second path; and if the peanut sample is classified as not suitable for protein powder processing, with the controller, sending a signal to the actuator to direct the peanut sample along a third path.

6. The method of claim 5, wherein the actuator is a component configured to direct the peanut sample along a processing path in processing equipment.

7. The method of claim 6, wherein the component is a sorting machine vane.

* * * * *